(12) United States Patent
Skibin et al.

(10) Patent No.: US 8,873,700 B2
(45) Date of Patent: Oct. 28, 2014

(54) METHOD FOR CORE THERMAL CONDUCTIVITY DETERMINATION

(75) Inventors: Aleksander Petrovich Skibin, Moscow (RU); Darya Aleksandrovna Mustafina, Perm (RU); Aleksandra Evgenievna Komrakova, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 322 days.

(21) Appl. No.: 13/519,878

(22) PCT Filed: Dec. 31, 2009

(86) PCT No.: PCT/RU2009/000758
§ 371 (c)(1),
(2), (4) Date: Oct. 12, 2012

(87) PCT Pub. No.: WO2011/081551
PCT Pub. Date: Jul. 7, 2011

(65) Prior Publication Data
US 2013/0094624 A1    Apr. 18, 2013

(51) Int. Cl.
*G01N 23/00*   (2006.01)
*G01N 23/04*   (2006.01)
*G01N 25/18*   (2006.01)
(52) U.S. Cl.
CPC .............. *G01N 23/046* (2013.01); *G01N 25/18* (2013.01)
USPC ............................................................ 378/4

(58) Field of Classification Search
CPC ............................ G01N 25/18; G01N 23/046
USPC ........... 378/4–20, 44, 45, 51, 53, 83; 382/131
See application file for complete search history.

(56) References Cited

U.S. PATENT DOCUMENTS 4,559,818 A    12/1985  Tsang et al.
7,086,484 B2    8/2006  Smith, Jr.

FOREIGN PATENT DOCUMENTS

RU           2189581 C2    9/2002

OTHER PUBLICATIONS

Vosteen, et al., "Influence of temperature on thermal conductivity, thermal capacity and thermal diffusivity for different types of rock", Physics and Chemistry of the Earth, Parts A/B/C, vol. 28 (9-11), 2003, pp. 499-509.
Patankar, S. V., "Numerical Heat Transfer and Fluid Flow", Hemisphere Publishing Corporation, Washington, 1st Edition, Jan. 1, 1980, pp. 59-61.

*Primary Examiner* — Courtney Thomas

(57) ABSTRACT

A method for core sample effective thermal conductivity provides for scanning a core sample by X-ray micro-computed tomography scanner and transferring a three dimensional scan image to an image analysis computer for processing. Then a layer thickness to be analyzed is set and a layer with maximum thermal resistance is defined within the image. The value of core effective thermal conductivity is defined by the allocated layer.

3 Claims, 4 Drawing Sheets

METHOD FOR CORE THERMAL CONDUCTIVITY DETERMINATION

CROSS-REFERENCE TO RELATED APPLICATIONS

This application is a United States National Stage Application under 35 U.S.C. §371 and claims priority to PCT Application Number PCT/RU2009/000758 filed Dec. 31, 2009, which is incorporated herein by reference in its entirety.

FIELD OF THE INVENTION

The present invention relates to the methods of measurement of thermophysical properties such as thermal conductivity of solid bodies, for example rocks.

BACKGROUND ART

Industrial application of thermal methods of oil recovery improvement implies prior simulation of heat and mass processes in reservoirs and wellbores as well as evaluation of thermal regime of downhole equipment. This fact raises the importance of problems concerned with the study of heat transfer in porous media (rock samples) that are composed of generally non-uniform solid skeleton and pores filled with one or several fluids—gases or liquids.

Thermal conductivity (TC) is normally measured in the laboratory on core, crushed samples, or well cuttings using one of two techniques: divided bar or needle probe (see, for example, H.-D. Vosteen, R. Schellschmidt "Influence of temperature on thermal conductivity, thermal capacity and thermal diffusivity for different types of rock", Physics and Chemistry of the Earth, 28 (2003), 499-509).

All these methods provides for thermal treatment of the samples followed by measurements. But heating is not desirable for liquid-filled samples since at heating the liquid partly vaporizes and forms gas locks inside the pore space which results in thermal conductivity error.

Physical models that were developed for effective TC calculation include three parameters: solid phase TC, saturating phase TC and microstructure of porous space. Ones the detailed internal microstructure of rock samples is obtained it become possible to determine the effective TC solving the thermal conductivity equation numerically (S. V. Patankar, 'Numerical Heat Transfer and Fluid Flow', Taylor&Francis, 1980, pp. 59-61). The direct numerical solution of thermal conductivity equation can be extraordinarily challenging when all the details of the complex 3D rock microstructure are accounted for. Sometimes it is impossible to apply this method because of significant expenses of computing time spent to perform calculations and incredibly expensive cost of computer resources needed for such simulations carrying out.

SUMMARY OF THE INVENTION

The proposed method allows fast estimation of effective thermal conductivity and does not require solving thermal conductivity equation numerically. This method relies only on core microstructure captured by the means of X-ray micro-computed tomography system (micro-CT) and comprises the steps of providing a core sample and an X-ray micro-computed tomography scanner (micro-CT) for scanning said core sample and generating an image for each scan, scanning said core sample, transferring the three dimensional scan images from the CT scanner to an image analysis computer for processing, setting a layer thickness to be analyzed, defining a layer with maximum thermal resistance within the produced three dimensional scan image and defining the core sample effective thermal conductivity.

The layer with maximum thermal resistance is a layer with the minimum total surface porosity.

The layer thickness to be analyzed is selected taking into account the core sample dimensions and the dimension of voxels.

DETAILED DESCRIPTION OF THE INVENTION

Digital rock models can be constructed from 2D thin sections, scanning-microCT, CT scans are 2-dimensional (2D) cross sections generated by an X-ray source that rotates around the sample. Density is computed from the X-ray attenuation coefficients. Scans of serial cross sections are used to construct 3D images of the sample. Because the density contrast is high between rocks and fluid-filled pores, CT images can be used to visualize the rock-pore system. Resolutions are on the sub-millimeter to micron scale, depending on the device being used.

X-ray computed tomography, or CT scan, is an important nondestructive core imaging technique. CT scans produce X-ray pictures of a series of contiguous equidistant 2D slices.

The present invention utilizes the following procedure to determine thermal conductivity of a core sample.

An X-ray CT scanner used is a third generation scanner where the source and detector are fixed and the scanned object rotates. A rock sample is placed on a turntable and horizontal X-ray beams generated from the X-ray source penetrate through the sample before they reach the detector. The source or sample is rotated by 360 degrees during the scan when the attenuated X-ray intensities are measured and the recorded attenuation profile of the slice can be transformed to a cross-sectional image. The sample is then shifted vertically by a fixed amount and the scan is repeated multiple times until the whole sample is imaged.

Figure 1:
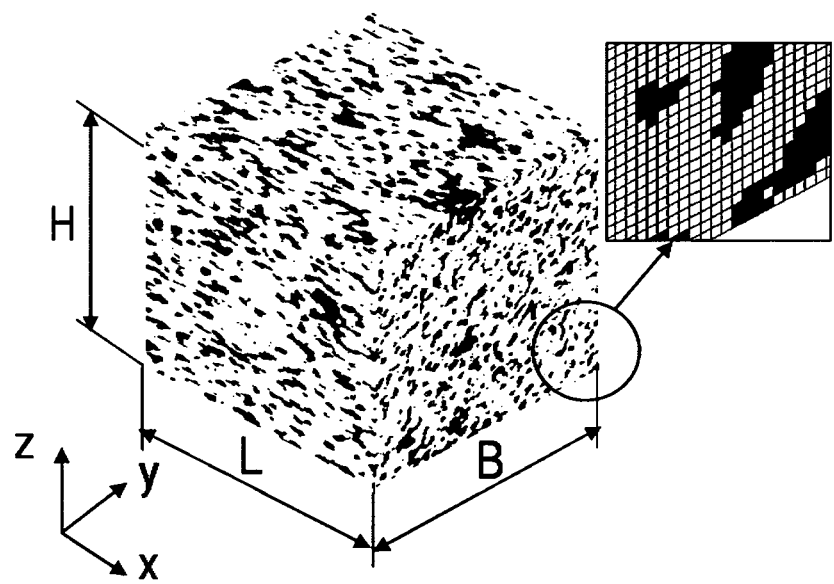
FIG. 1 shows a microstructure of a core sample captured by the means of X-ray micro-CT.

A structure of the core sample, which structure has been obtained using micro-CT, is shown in FIG. 1. White color corresponds to a skeleton of porous media while black color represents fluids that remain in pores. It is assumed that thermal contact between porous media cells is ideal. Physical properties of skeleton and fluid are constant and all pores are filled with the fluid.

This scanned image is then transferred to an image analysis computer for processing.

The layer with maximum thermal resistance defines thermal flux. Therefore, it is necessary to find the layer with maximal thermal resistance. The criterion for the search is minimum surface porosity of the allocated layer.

Figure 2:
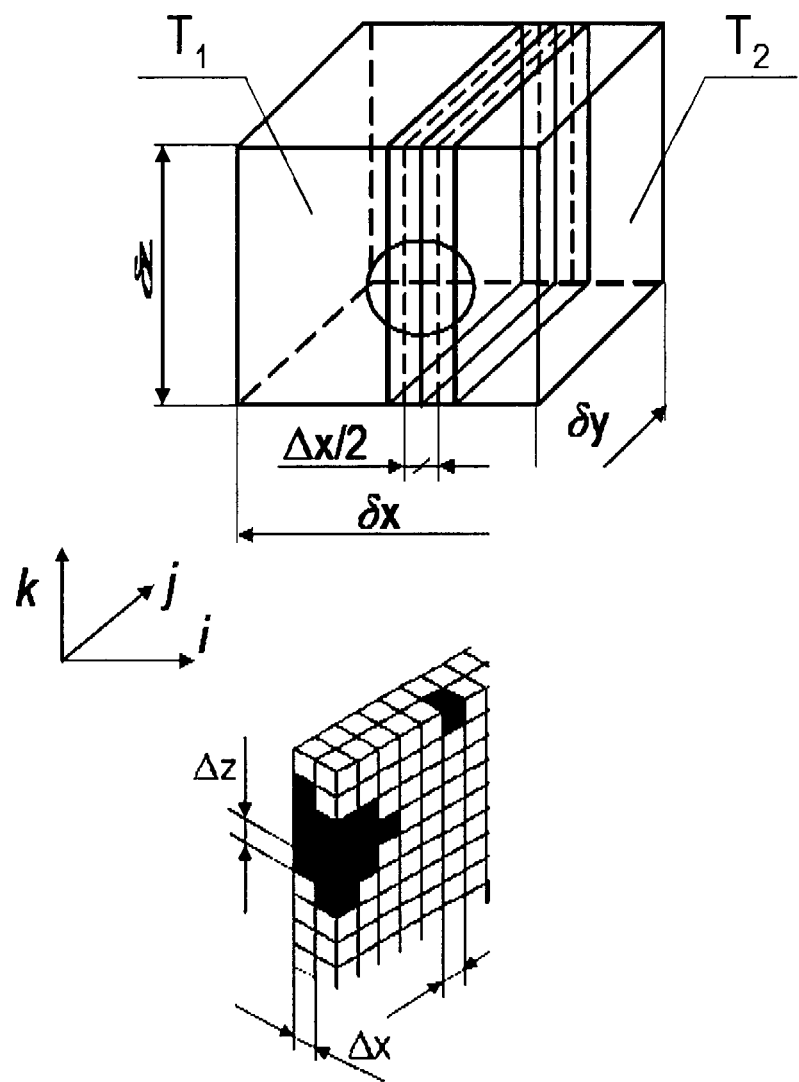
FIG. 2 illustrates an example of a layer with maximum thermal resistance with number of cell m=2.

In order to describe the suggested method of core TC estimation, a case is considered where an allocated layer consists of two cells in the direction of heat conduction (FIG. 2). It is assumed that heat conduction takes place only in one direction (along X axis) and a temperature gradient on the sample length is constant, i.e., $$\frac{\Delta T}{\Delta x} = \frac{\delta T}{\delta x}, \quad (1)$$

where $\Delta x$ is voxel resolution in axis X direction, m; $\delta T=T_2-T_1$, where $T_1$ and $T_2$ are values of temperature on opposite sample faces which are perpendicular to X axis, K.

The dimensions of sample (FIG. 2) can be determined as follows:

$$\delta x \Delta x \cdot N_x, \; \delta y = \Delta y \cdot N_y, \; \delta z = \Delta z \cdot N_z,$$

where $\Delta y$, $\Delta z$ are voxel resolution in direction of Y and Z axis, m; $N_x$, $N_y$ and $N_z$—number of cells along X, Y and Z axis, correspondingly.

The value of thermal flux in X direction through two contiguous cells with indexes (j;k) endwise Y and Z axis is determined by the following formula:

$$q_{jk} = \frac{\delta T}{N_x \left( \frac{\Delta x}{2\lambda_1^{jk}} + \frac{\Delta x}{2\lambda_2^{jk}} \right)} \Delta y \Delta z, \quad (2)$$

where $\lambda_1^{jk}$ and $\lambda_2^{jk}$ are the TCs of cells in allocated layer. Here the indexes 1 and 2 refer to the first and the second cells of allocated layer in X direction, respectively. The expression (2) can be transformed to the following view:

$$q_{jk} = \frac{\lambda_1^{jk} \cdot \lambda_2^{jk}}{\lambda_1^{jk} + \lambda_2^{jk}} \frac{2\delta T}{N_x} \frac{\Delta y \Delta z}{\Delta x} \quad (3)$$

Thermal heat flux through all allocated cells layer in the X direction is calculated in the following way:

$$Q_x = \sum_{j=1}^{N_y} \sum_{k=1}^{N_z} q_{jk} = \frac{2\delta T}{N_y N_z} \frac{\delta y \delta z}{\delta x} \sum_{j=1}^{N_y} \sum_{k=1}^{N_z} \lambda_{ef}^{jk} \quad (4)$$

where $$\lambda_{ef}^{jk} = \frac{\lambda_1^{jk} \cdot \lambda_2^{jk}}{\lambda_1^{jk} + \lambda_2^{jk}}$$

is effective TC in X direction of two contiguous cells with equal indexes (j;k) endwise Y and Z axis.

From the other side, thermal flux through the sample in the X direction is determined by expression:

$$Q_X = \lambda_{ef\_X} \frac{\delta T}{\delta x} \delta y \delta z, \quad (5)$$

If we equate formulas (4) and (5), we will define effective TC as follows:

$$\lambda_{ef\_X} = \frac{2}{N_y N_z} \sum_{j=1}^{N_y} \sum_{k=1}^{N_z} \lambda_{ef}^{jk} \quad (6)$$

Transformation of expression (6) gives:

$$\lambda_{ef\_X} = \phi_1 \lambda_s + \phi_2 \lambda_{fl} + \frac{2\phi_{12}}{\frac{1}{\lambda_s} + \frac{1}{\lambda_{fl}}}, \quad (7)$$

After making (6) dimensionless it takes the following form:

$$\hat{\lambda}_{ef\_X} = \phi_1 + \phi_2 \hat{\lambda}_f + \frac{2\phi_{12}}{1 + \frac{1}{\hat{\lambda}_f}}, \quad (8)$$

where $\phi_1$, $\phi_{12}$ and $\phi_2$ are surface parts of filling of considered layer only with rock core, rock core together with fluid and only with fluid correspondingly. The values of quantities $\phi_1$, $\phi_{12}$ and $\phi_2$ are defined with the following expressions:

$$\phi_1 = \sum_{jk} \frac{C_{jk}}{N_y N_z}, \; C_{jk} = \begin{cases} 1, \lambda_1^{jk} = 1, \lambda_2^{jk} = 1 \\ 0, \lambda_i^{jk} \neq 1, i = 1, 2 \end{cases}$$

$$\phi_2 = \sum_{jk} \frac{C_{jk}}{N_y N_z}, \; C_{jk} = \begin{cases} 1, \lambda_1^{jk} = \lambda_2^{jk} = \hat{\lambda}_f \\ 0, \lambda_i^{jk} \neq \hat{\lambda}_f, i = 1, 2, \end{cases}$$

$$\phi_{12} = 1 - \phi_1 - \phi_2.$$

The quantity $\phi_1$ is also used in order to determine the minimum total surface porosity of allocated layer—$\epsilon$. For this purpose the following term is used:

$$\epsilon = 1 - \phi_1 \quad (9)$$

Now, a case is considered where an allocated layer consists of m cells in the X direction and m is an odd number. In this case, a temperature difference between the medium of first and last cells of allocated layer are defined as:

$$\Delta T_m = (m-1)\frac{\delta T}{N_x}$$

Then thermal flux through the layer from m cells is calculated as follows:

$$q_{jk} = \lambda_{ef\_X}^{jk} \frac{\Delta T_m}{\Delta x} \cdot \Delta y \cdot \Delta z = \lambda_{ef\_X}^{jk} \frac{(m-1)\delta T}{N_x} \frac{\Delta y \Delta z}{\Delta x}$$

Here $\lambda_{ef\_X}^{jk}$ is effective TC of "column" that contains m cells in X direction:

$$\lambda_{ef\_X}^{jk} = \frac{1}{\frac{1}{2\lambda_1^{jk}} + \frac{1}{2\lambda_m^{jk}} + \sum_{i=1}^{m-1} \frac{1}{\lambda_i^{jk}}}$$

Then thermal flux through layer with thickness equal to m cells in X direction is defined as given below:

$$Q_X = \frac{(m-1)\delta T}{N_y N_z} \frac{\delta y \delta z}{\delta x} \sum_{j=1}^{N_y} \sum_{k=1}^{N_z} \lambda_{ef\_X}^{jk} \quad (10)$$

Using expressions (5) and (10) and making several transformations the result term for effective TC determination for layer containing m cells in X direction can be written as follows:

$$\lambda_{ef\_X} = \frac{(m-1)}{N_y N_z} \sum_{j=1}^{N_y} \sum_{k=1}^{N_z} \lambda_{ef\_X}^{jk} \quad (11)$$

The estimation of TC using proposed method has been done for a sample of 240×240×240 voxels. The comparison of calculated TC with precise solution has shown that the error of estimation does not exceed 3.6% for a considered sample.

Figure 3:
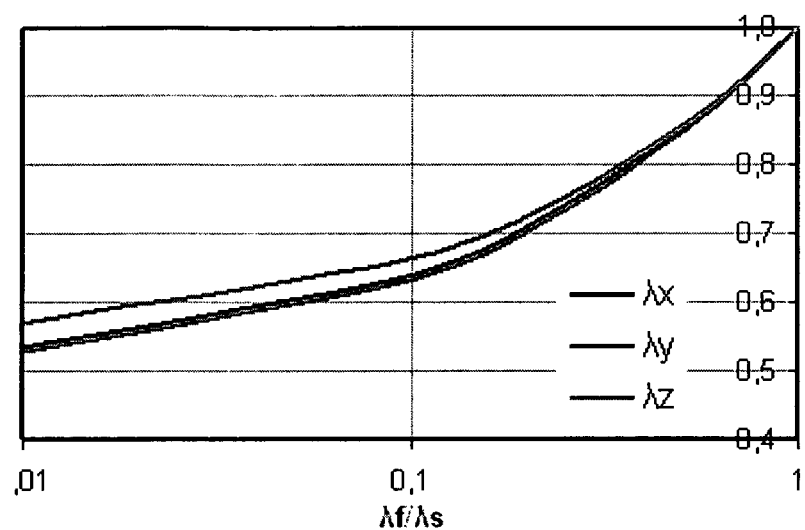
FIG. 3 shows relative components of effective TC tensor vs relative TC of saturating phase for the $1^{st}$ core sample of 1800×1800×1800.

With the use of proposed method the determination of tensor components of relative effective TC was carried out for two core samples with the size of 1800×1800×1800 voxels. For the first sample, the variation of allocated layer thickness was made in a direction perpendicular to heat conduction. The interval of variation was from 3 to 21 cells, while the layer thickness changed from 15 to 105 microns. The influence of layer thickness for sample saturated with air and water was studied. For this sample, the optimal thickness of allocated layer was 11-15 cells. In this case, an error of effective TC determination using approximate method as compared with upscaling procedure was not more than 5%. So, in order to estimate TC of core samples with size 1800×1800×1800 voxels and cell dimension in 5 microns, the allocated layer thickness is set to 13 cells. FIG. 3 shows the dependencies of relative tensor components of effective TC from the relative TC of saturating phase $\hat{\lambda}_f$. While choosing the allocated layer thickness in 13 cells the relative error of proposed method is not more than 1.5%.

Figure 4:
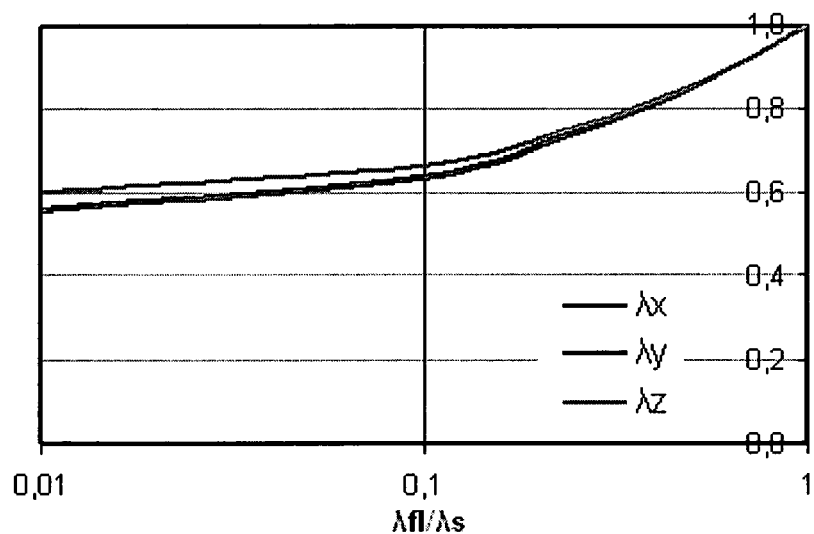
FIG. 4 shows relative components of effective TC tensor vs relative TC of saturating phase for the $2^{nd}$ core sample of 1800×1800×1800.

The dependence of effective TC tensor components from relative TC of saturating medium for the second sample is presented in FIG. 4. The error of components of effective TC tensor determination for second sample is less than 6%.

The duration of numerical estimation of effective TC tensor components for one sample with size in 1800×1800×1800 cells was in the order of 1000 seconds of CPU time.

The invention claimed is:

1. A method for determining effective core sample thermal conductivity, the method comprising:
providing a core sample and an X-ray micro-computed tomography scanner for scanning said core sample and generating an image for each scan,
scanning said core sample using the scanner to generate a three dimensional scan image,
transferring said three dimensional scan image from the scanner to an image analysis computer for processing,
setting a layer thickness within the produced three dimensional scan image to be analyzed,
defining a layer with maximum thermal resistance within the produced three dimensional scan image, and
defining effective thermal conductivity for the core sample.

2. The method of claim 1 wherein the layer with maximum thermal resistance is a layer with the minimum total surface porosity.

3. The method of claim 1 wherein the layer thickness to be analyzed is selected taking into account the core sample dimensions and the dimension of voxels.

* * * * *